United States Patent [19]

Ales

[11] Patent Number: 5,488,959
[45] Date of Patent: Feb. 6, 1996

[54] MEDICAL GUIDEWIRE AND WELDING PROCESS

[75] Inventor: Francisco Ales, Hialeah, Fla.

[73] Assignee: Cordis Corporation, Miami Lakes, Fla.

[21] Appl. No.: 173,788

[22] Filed: Dec. 27, 1993

[51] Int. Cl.⁶ ............................................. A61B 5/00
[52] U.S. Cl. ............................................. 128/772; 128/657
[58] Field of Search ................ 29/606; 228/126, 228/130, 136, 218, 262.3, 262.31, 262.71, 262.72; 128/657, 772

[56] References Cited

U.S. PATENT DOCUMENTS

| | | | |
|---|---|---|---|
| Re. 33,911 | 5/1992 | Samson et al. | 128/772 |
| 3,528,406 | 9/1970 | Jeckel et al. | |
| 3,753,700 | 8/1973 | Harrison et al. | |
| 3,789,841 | 2/1974 | Antoshkiw | |
| 3,906,938 | 9/1975 | Fleischhacker | |
| 4,283,233 | 8/1981 | Goldstein et al. | |
| 4,538,622 | 9/1985 | Samson et al. | 128/772 |
| 4,619,274 | 10/1986 | Morrison | 128/772 |
| 4,665,906 | 5/1987 | Jervis | 128/92 YN |
| 4,721,117 | 1/1988 | Mar et al. | 128/772 |
| 4,763,647 | 8/1988 | Gambale | 128/657 |
| 4,813,434 | 3/1989 | Buchbinder et al. | 128/772 |
| 4,846,186 | 7/1989 | Box et al. | 128/687 |
| 4,925,445 | 5/1990 | Sakamoto et al. | 604/95 |
| 4,969,890 | 11/1990 | Sugita et al. | 606/192 |
| 4,984,581 | 1/1991 | Stice | 128/772 |
| 5,069,226 | 12/1991 | Yamauchi et al. | 128/772 |

FOREIGN PATENT DOCUMENTS

| | | |
|---|---|---|
| 141006 | 5/1985 | European Pat. Off. |
| 376132 | 7/1990 | European Pat. Off. |

OTHER PUBLICATIONS

Shape Memory and Super-elasticity Effects in NiTi Alloys.

*Primary Examiner*—Sam Rimell
*Attorney, Agent, or Firm*—Lockwood, Alex, Fitzgibbon & Cummings

[57] ABSTRACT

A process is provided which is particularly suitable for manufacturing medical guidewires. The resulting products have a weld that has good pull strength and is of minimum brittleness even when one of the components being welded together is a fine wire of material that is susceptible to damage and severe deterioration when subjected to harsh heating conditions. The invention is particularly suitable when that material is a Nitinol alloy. The process supports the other component to be welded such as a coil within a collet such that a substantial portion of it projects beyond the collet and is not supported thereby. A heat source renders this projecting portion molten, after which the other component made of Nitinol, for example, is embedded into the molten mass, usually still under the influence of the heat source, to thereby effect a joining which, after cooling, provides the improved weld without imparting brittleness to either component.

21 Claims, 3 Drawing Sheets

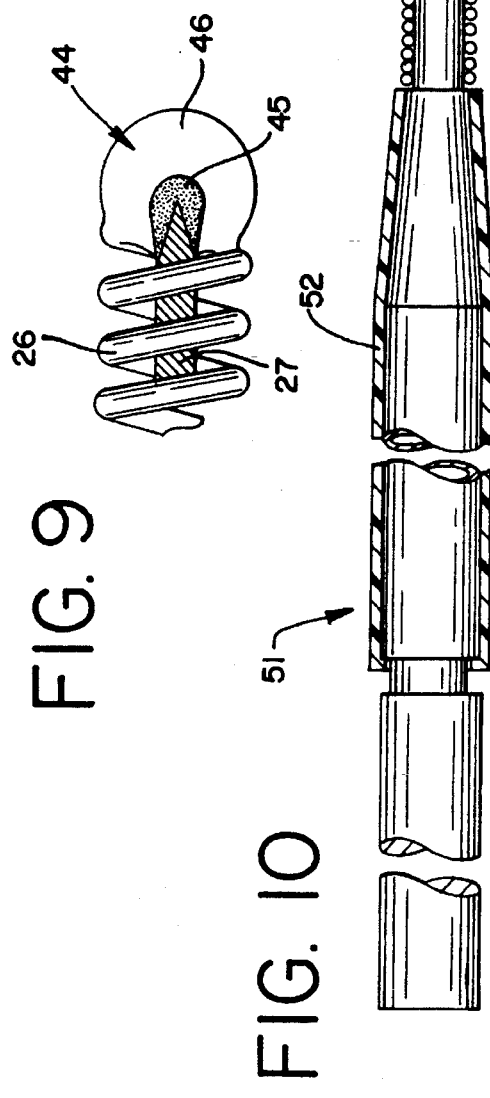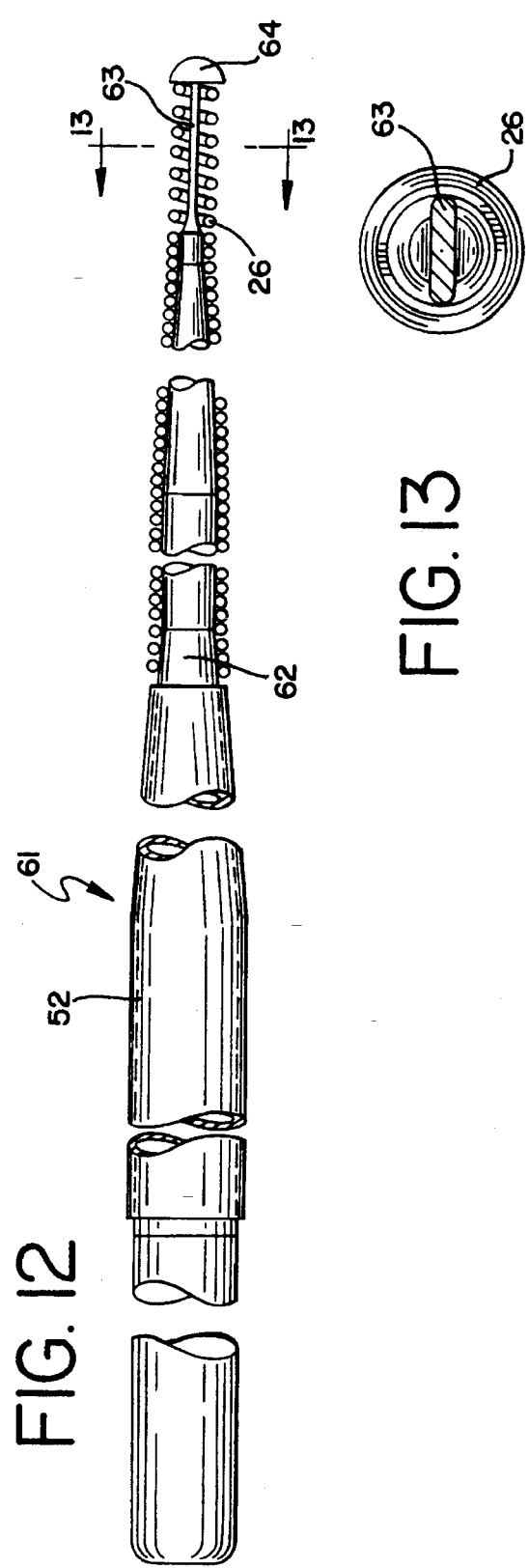

1

MEDICAL GUIDEWIRE AND WELDING PROCESS

BACKGROUND AND DESCRIPTION OF THE INVENTION

The present invention generally relates to guidewires for use with medical catheters and to a welding procedure useful in manufacturing guidewires and other devices incorporating welding techniques. The welding procedure is particularly well-suited for assembling guidewire core wires of an alloy containing nickel and titanium as the principal components with a component such as a guidewire coil made of a different metal or material. Such an assembly procedure is in the nature of welding, and in the context of a medical guidewire, the weld forms the distal tip of the guidewire from the guidewire tip coil and the distal end of the core wire.

Guidewires have long been used in many medical procedures. Generally speaking, a guidewire is the initial member inserted into a body cavity during many transluminal procedures. A guidewire is an elongated fine wire device that is intended to readily pass through body passageways and to a location at which a medical procedure or treatment is to take place. Thereafter, in a typical arrangement, a catheter is slid over the thus inserted guidewire, with the catheter following the pathway defined by the guidewire. In general terms, a guidewire is flexible, at least at its remote distal end tip.

Remote distal end tip flexibility is often enhanced by providing a fine coil at the distal portion of the guidewire and securing that fine coil, typically at its distal end, to the distal end of the core wire of the guidewire. Typically, this securement application also includes a rounded distal tip that imparts some atraumatic characteristics to the guidewire. In the usual approach, these components are secured together by soldering, brazing, welding or by the use of an adhesive such as ultraviolet-curing adhesives or anaerobic adhesives such as cyanoacrylate adhesives.

It will be appreciated that core wires and guidewire coils are of extremely small diameter and are particularly fine and difficult to assemble by whatever means are utilized. Welding can be especially troublesome, particularly when attempting to work with certain materials that can be difficult to weld together. In this regard, it has been proposed to manufacture guidewires or other devices which incorporate components made of so-called shape memory alloys such as nickel and titanium alloys. Included are the so-called Nitinol alloys. Welding of these materials has met with considerable difficulty. Welding in accordance with conventional techniques has led to the development of embrittlement at the weld area, particularly of a Nitinol component. Materials such as Nitinol have been found to be so sensitive that they become embrittled when subjected to conditions that are too harsh.

It has been found that the procedure in accordance with the present invention provides welds of guidewires and other devices that minimize these types of embrittlement problems, even when a component being welded is made of a Nitinol material. In summary, the present invention accomplishes this improved welding by a procedure which includes inserting a guidewire coil or the like into a collet such that a distal end portion of the coil or the like projects out of the collet and beyond its face, and locating an elongated core wire or the like at a staged position remote from this face of the collet. Next, the projecting distal end portion of the coil is heated in order to form a heated tip mass until this mass engages the face of the collet, preferably in substantially sealed engagement. Then, this heated tip mass and the leading end of the core wire or the like are engaged with each other, typically by sliding the core wire or the like along the axis of the coil or the like and into the heated tip mass. Upon cooling, the leading end is joined to the now solidified coil tip mass so as to define a welded assembly. This welded assembly is suitable for use as a coil and core wire of a medical guidewire joined together by a generally atraumatic tip formed from the heated tip mass. This procedure and the products produced thereby are especially suitable for welding when one of the components, such as a core wire component, is made of a Nitinol alloy of which nickel and titanium are the principal components.

It is a general object of the present invention to provide an improved medical guidewire and welding process.

Another object of this invention is to provide an improved welding process, particularly suitable for medical devices, that avoids imparting harsh conditions to at least one of the components welded together, the procedure finding special application when one of the components is a Nitinol type of alloy.

Another object of the present invention is to provide an improved medical guidewire with a heat-formed distal tip having a core wire welded therewithin, which core wire is of a material that is particularly sensitive to deterioration when subjected to excessively high welding temperatures.

Another object of the present invention is to provide an improved process for manufacturing, including a procedure for welding a Nitinol elongated component together with another assembly component having a melting temperature greater than the Nitinol alloy.

These and other objects, features and advantages of this invention will be clearly understood through a consideration of the following detailed description.

BRIEF DESCRIPTION OF THE DRAWINGS

The invention will be further elucidated in the following description with reference to the drawings in which:

FIG. 9 is a detail view, partially in cross-section, of a preferred welded assembly made in accordance with the present invention;

FIG. 10 is an elevational view, partially in longitudinal cross-section, of an embodiment of a guidewire in accordance with this invention;

FIG. 11 is a cross-sectional view along the line 11—11 of FIG. 10;

FIG. 12 is a longitudinal view, partially broken away, with the coil being shown in cross-section, of an alternate embodiment of a guidewire in accordance with the present invention; and FIG. 13 is a cross-sectional view along the line 13—13 of FIG. 12.

DESCRIPTION OF THE PARTICULAR EMBODIMENTS

Figure 1:
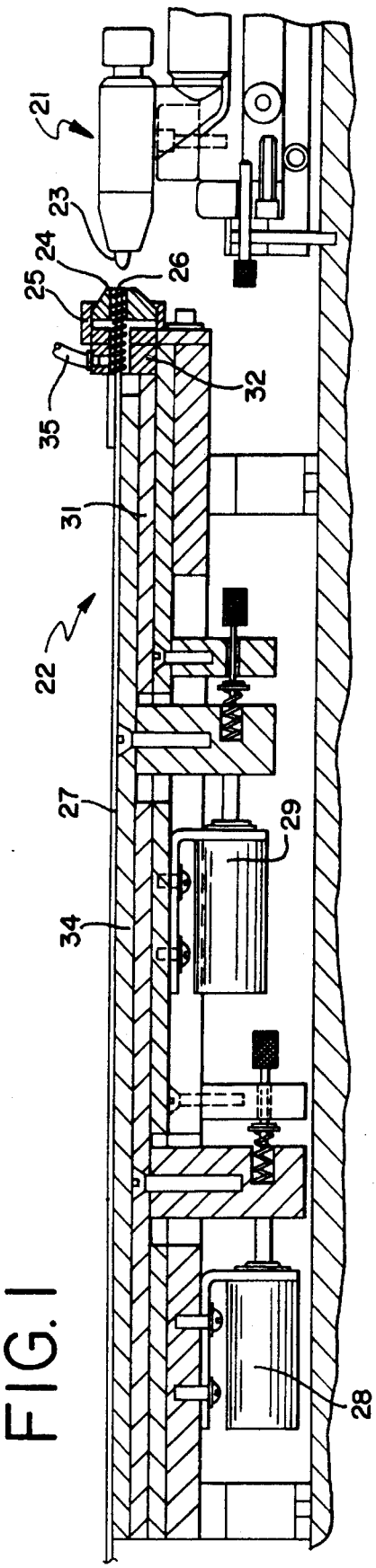
FIG. 1 is an elevational view of an apparatus suitable for carrying out the procedure in accordance with the present invention.
Figure 2:
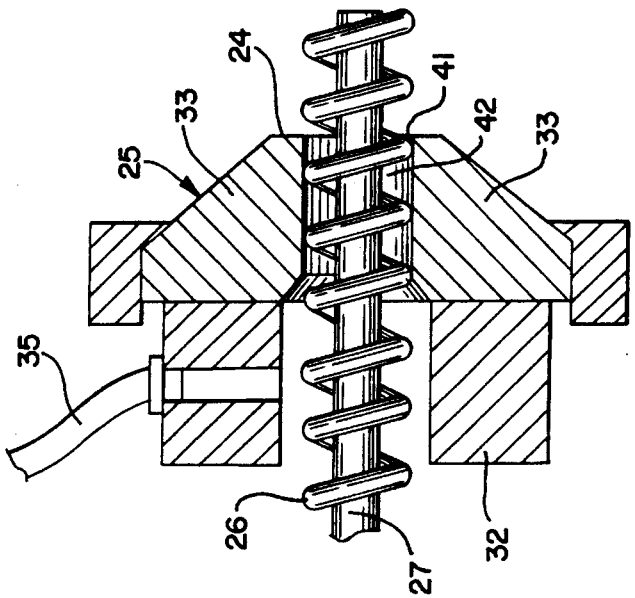
FIG. 2 is an enlarged cross-sectional view through the collet assembly illustrated in FIG. 1 and showing a guidewire coil held thereby and a core wire coaxial with the coil.
Figure 3:
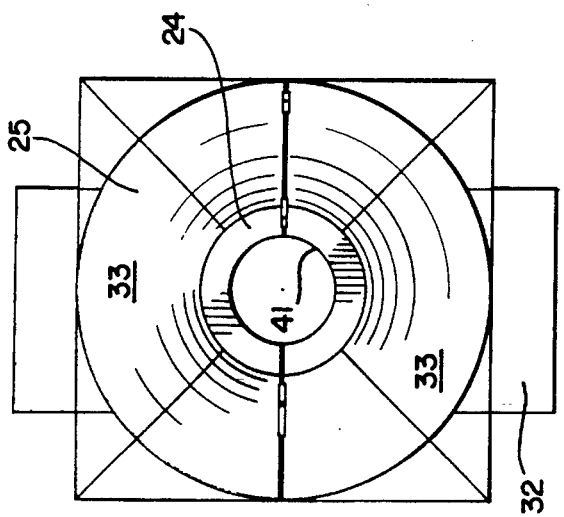
FIG. 3 is an enlarged end view detailing a collet portion of an apparatus such as that illustrated in FIGS. 1 and 2.

Referring first to the apparatus that is illustrated for carrying out the present invention, FIG. 1 shows a heat source assembly, generally designated at 21, and a support and presentation fixture 22. Heat source assembly 21 incorporates a known type of heating equipment that directs heat, such as from or around a nozzle 23, toward the fixture 22, more specifically toward the face 24 of a collet 25 mounted on the fixture 22. In this manner, heat source assembly 21 provides a source of heat that is capable of rendering molten parts or components that are held by the collet 25.

Fixture 22 functions to hold in place a coil component 26 and to move an elongated core wire 27 in a carefully timed manner and under precise movement conditions. In the illustrated embodiment, these functions are performed by sliding operations, although various other specific means are possible. Preferably, the sliding motion is effected by suitable control movement assemblies 28, 29, which are illustrated generally schematically and can include solenoids, stepper motors and timing controllers to effect two basic functions. One of the functions is opening and closing of the collet 25 so as to properly position the coil component 26 and release the welded assembly after formation thereof. The other function is timed movement of the core wire 27, including movement from a staged position spaced well away from the face 24 of the collet 26 and to a joining position at which the leading end of the core wire is generally at the face 24 of the collet 25.

Again, in accordance with the general illustration of a suitable apparatus for carrying out the present invention that is illustrated in FIG. 1, the control movement assembly 28 slidingly moves a plate 31 that engages a collar 32 for opening and closing jaws 33 of collet 25 in a manner generally known in the art. In a generally similar manner, the control movement assembly 29 slidingly moves a plate 34 onto which the core wire 27 is securely mounted. With this arrangement, activation of the control movement assembly 29 moves the core wire 27 while the coil component 26 remains stationary and supported within the collet 25.

The support and presentation fixture 22 also includes a gas injector arrangement 35 which can be used to bathe the collet area with a cooling gas. Suitable cooling gases include argon, helium, combinations thereof or the like. The gas injector feeds this cooling gas from behind the collet and floods the welding locations to minimize or even prevent air and possible contaminating components such as oxygen and hydrogen from deleteriously affecting the weld. When the cooling gas flows through the gas injector 35, contaminants are displaced from the welding environment inside the collet, including its passageway 42. It also serves to provide a pressure flow to prevent any welding gas from reaching the tip of the core wire inside the collet assembly and from entering the collet assembly in the vicinity of its face 24.

With more particular reference to the heat source assembly 21, this can take the form of a plasma arc welder, a laser welder, and other closely controllable, both from the point of view of temperature and heat propagation direction, heat supply. It is generally preferred that the welding be conducted within an atmosphere that will minimize or eliminate the chance of airborne contamination. Use of the gas injector arrangement 35 as generally discussed herein is instrumental in achieving this objective. When the heat source utilizes a gaseous medium, selection of an appropriate medium is also useful in this regard. Appropriate media for procedures such as plasma arc welding or laser welding include the inert gases, with argon being especially preferred. Combinations of inert gases including argon, helium and other inert gases of reasonable cost, can also be used. When plasma arc welding is employed, an electric welder is used, and a voltage differential or potential is developed between the nozzle and the coil component 26. A very small arc is created, and the excited welding gas is responsible for formation of a more elongated arc which bridges the gap between the nozzle 23 and the coil component 26. The conditions are such that the heat source assembly increases the temperature of the coil component in order to render it molten.

Figure 4:
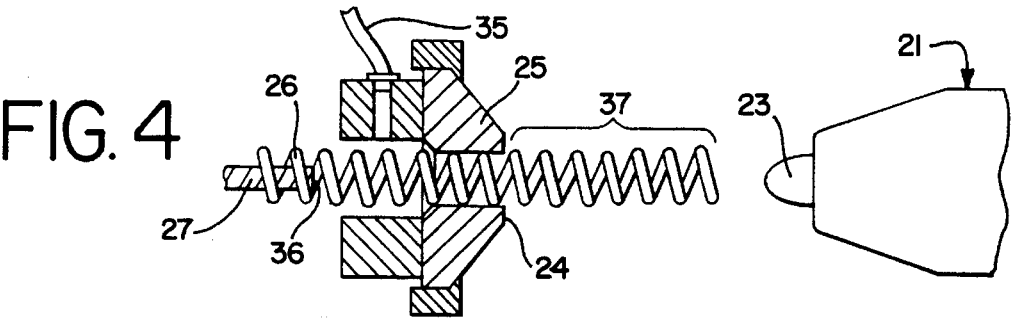
FIGS. 4 through 8 are somewhat schematic views that illustrate successive steps of the welding procedure according to the invention.

FIG. 4 illustrates an initial stage of the welding procedure in accordance with the invention. Core wire 27 is at a staged position wherein its leading end 36 is spaced well away from the collet 25 and particularly its face 24. It will also be noted that the coil component 26 is securely supported by the collet in a manner such that a substantial number of the turns of the coil component 26 project out of the collet 25 or beyond its face 24 in order to define a coil projecting length 37 that is generally adjacent to and opposes the heat source assembly 21.

Figure 5:
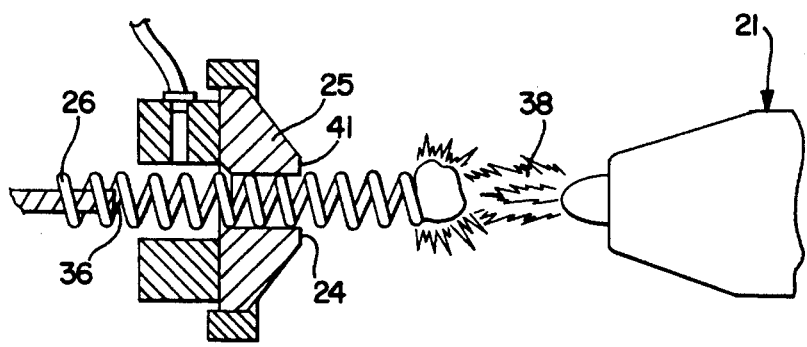
Figure 6:
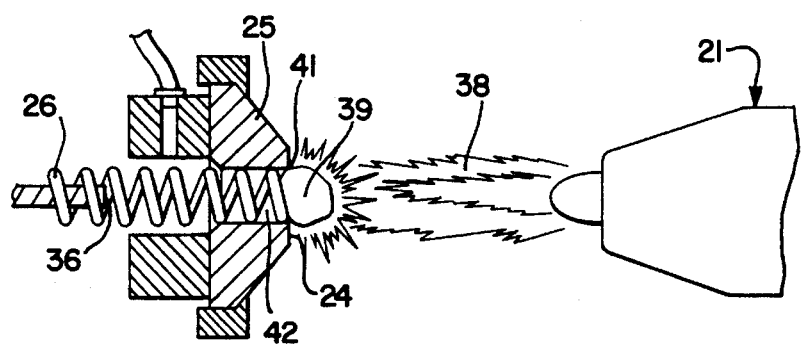

Next, heat source assembly 21 is energized, as generally illustrated in FIG. 5. As a result, the heat transmission medium 38 begins to melt or render molten the coil projecting length, almost immediately beginning to shorten same and move it in a direction toward the collet face 24. This heat supplying operation continues until the coil projecting length 37 is transformed into a heated tip mass 39 (FIG. 6). The conditions and equipment are arranged such that the heated tip mass engages the collet 25. In the especially preferred arrangement, the heating is continued under the proper conditions such that the heated tip mass 39 engages a peripheral inside edge 41 of the collet face. In accordance with this arrangement, the entire circumference of the collet face edge 41 is engaged by the heated tip mass 39 in order to thereby seal collet passageway 42 from the heat source such as illustrated flame 38. This condition is generally shown in FIG. 6.

Figure 7:
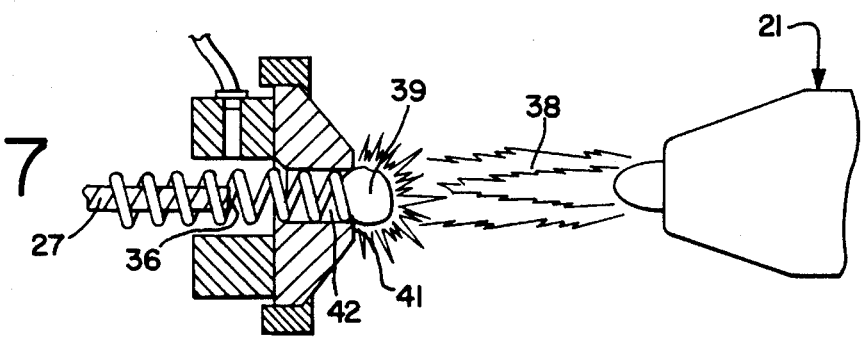
Figure 8:
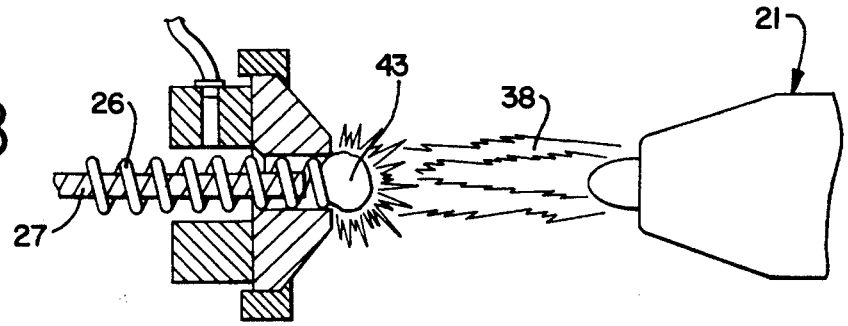

With the condition shown in FIG. 6 having been attained, the time is now right for the core wire 27 to begin moving away from its staged position and toward the collet face 24 and the heated tip mass 39, preferably while maintaining the heat source in operation as illustrated in FIG. 7. Movement of the core wire 27 continues until its leading end 36 engages and enters into the heated tip mass 39, as generally shown in FIG. 8. At this time, the heated tip mass is transformed into a heated tip assembly 43. Heat source can remain activated during this formation procedure, as generally shown in FIG. 8.

Upon cooling, the heated tip assembly 43 becomes a welded assembly, an exemplary Welded assembly being generally designated at 44 in FIG. 9. Here, the molten heated tip mass 39 which originated from the coil component 26 had melted the core wire 27 to effect the welding operation. Under the appropriate conditions, the resulting welded assembly 44 includes a metal interchange portion 45 generally positioned at the transition location between the cooled and solidified coil component mass 46 and the adjoining portion of the core wire 27. Whether a distinct metal interchange portion 45 is formed or not, the welded assembly 44 will generally include the feature of having an enlarged end of the core wire 27 within the coil component mass 46. This enlarged end portion, which is generally designated at 45 in FIG. 9, provides a lock mechanism whereby good pull strength of the assembly 44 is experienced because the enlarged tip creates a lock mechanism to maintain the assembly together.

Guidewires of the type that can incorporate the principles of the present invention are illustrated in FIGS. 10, 11, 12 and 13. One embodiment of such a guidewire is generally designated as 51 in FIG. 10. The elongated core wire 27 has a stepped construction wherein it varies in diameter throughout its length. The coil component 26 is also shown. Respective distal tip ends of the coil component and the core wire are secured together by means of the welded assembly 44 as described herein. A portion of the elongated core wire can be covered with a polymeric sleeve 52. Typically, sleeve 52 is made of a lubricious material and is provided in order to reduce potential trauma during insertion into the patient. The various illustrated tapered portions of the core wire 27 are typically formed by centerless grinding in order to form the various portions of the tapering distal length as illustrated.

FIGS. 12 and 13 illustrate another embodiment of a guidewire, generally designated as 61, which can incorporate the present invention. In addition to differences in the tapering configuration of its core wire 62, the distal end of the core wire of this embodiment is of a flattened variety in order to thereby provide a ribbon tip 63. The ribbon tip 63 is formed by flattening the desired length of the distal end portion of the core wire by a procedure in which force is applied to the core wire at this location until it is flattened to the cross-section generally shown in FIG. 13. The cross-sectional height of this ribbon tip 63 is substantially less than its cross-sectional width, as best seen in FIG. 13. It will be appreciated that the core wire 62, including its flattened ribbon tip 63, can be made of a unitary piece of metal. The distal end portion of the coil 26 and the distal end portion of the ribbon tip 63 form a welded assembly 64 made in accordance with the welding procedure discussed herein.

Guidewires as discussed herein can have core wires made of various materials such as stainless steel and other alloys. In the preferred embodiment of the guidewires discussed herein, the core wire is constructed of an alloy including nickel and titanium. These are generally categorized as Nitinol alloys. These alloys have been found to be particularly useful for preparing guidewires having especially advantageous flexibility and malleability because they can be readily bent by the physician prior to insertion in order to impart a desired end shape to the guidewire, such as a J-shape. Once bent, the tip portion in accordance with the invention can be straightened and bent again without the development of any noticeable kinking at the bending locations. Core wires made of stainless steel, for example, exhibit kinking when bent and straightened to the extent that it typically is not possible to fully eliminate a bend before the rebending to the more desired shape. This can be important, for example, when the physician makes an initial bend that is not satisfactory. In this instance, the guidewire tip in accordance with the present invention is readily bent back to its original configuration (such as a straight configuration). Thereafter, the physician can proceed with a second bend until the desired tip configuration is prepared.

Generally speaking, Nitinol materials exhibit an original heat stable configuration, or austenite condition, and a heat unstable configuration, or martensite condition. Such shape memory alloys move from the austentic state to the martensitic state when the temperature of the alloy is lowered to the particular transition temperature for that alloy. Transformation from the martensitic state to the austentic state is effected by raising the temperature of the alloy beyond an appropriate transition temperature. Alloys of this type are typically characterized by austentic temperature values. The temperature at which the alloy begins to revert back to the austentic state is referred to as the $A_s$ temperature, while the temperature at which this reversion is complete is referred to as the $A_f$ temperature. The alloys containing nickel and titanium which are preferred in accordance with the present invention exhibit an austentic temperature greater than about 10° C. and not greater than about 20° C. Such devices do not undergo temperature-induced shape changes normally associated with shape memory alloys at the temperatures to which the guidewire is subjected during normal use, including warm-blooded body temperatures and room temperature.

Nitinol corewires can be made as an alloy including nickel and titanium in somewhat equal proportions. These preferred alloys are primarily composed of nickel and titanium, although low levels of other metals can be included. Typical Nitinol alloys can have about 50% of each of nickel and titanium, plus or minus about 8% of each. An exemplary Nitinol is one having about 55.9% nickel and about 43.9% titanium, while another such alloy has between about 49.5% nickel and about 50.5% titanium.

Concerning the coil component 26, it is preferably a platinum or platinum alloy helical coil. While such materials are preferred, in some instances it may be desired to use metals such as tantalum, stainless steel and the like. An exemplary platinum coil is a platinum and tungsten alloy comprised of approximately 92 weight percent platinum and approximately 8 weight percent tungsten. Materials of this type are less susceptible to heat damage than are Nitinol alloys. Also, the platinum alloys generally will have a melting point greater than that of the Nitinol alloys so that the molten platinum of the heated tip mass will melt the Nitinol of the core wire during the welding procedure. This melting temperature is maintained in accordance with the invention by continuing to impart heat energy to the heated tip mass prior to and during movement of the leading end of the core wire to and into the heated tip mass.

Generally, irrespective of the specific materials out of which the two components to be welded together are to be made, the process finds special application when, as is the case for Nitinol core wire and a platinum helical coil, the melting point of one component is greater than the melting point of the other component. The mounted component typically has a melting point substantially greater than that of the component which is moved thereinto. Preferably, this difference in melting points is equal to or greater than 100° C.

In the past, when attempting to join a platinum coil with a Nitinol core wire at their respective distal tips, a soldering approach, rather than a welding approach, has been utilized with some success. However, the soldering operation is extremely tedious and time-consuming. For example, such a soldering operation at one station can produce on the order of 50 assembled pieces per 8-hour shift. The welding procedure in accordance with the present invention is able to securely weld together the distal tip portions of a platinum coil and a Nitinol core wire at the rate of about 50 pieces per hour. Accordingly, it will be seen that the present invention is of a substantially higher speed than the more laborintensive and tedious soldering approach used heretofore.

It will be understood that the embodiments of the present invention which have been described are illustrative of some of the applications of the principles of the present invention.

Various modifications may be made by those skilled in the art without departing from the true spirit and scope of the invention.

I claim:

1. A process for manufacturing a medical guidewire, the process including a procedure for providing an assembly of a core wire and a coil generally coaxial with each other, the procedure comprising the steps of:

inserting a guidewire coil into a collet to thereby support the guidewire, said inserting step including projecting a distal end portion of the coil beyond a face of the collet such that the distal end portion of the coil is not in engagement with the collet and extends therebeyond;

locating an elongated core wire at a staged position remote from and at a location behind the face of the collet, the core wire having a leading end;

heating the distal end portion of the coil in order to form a heated tip mass, and continuing the heating until the heated tip mass engages the face of the collet;

effecting relative movement between the coil and the core wire at its staged position until the core wire is at a location within the coil supported by the collet, said effecting step including engaging the leading end of the core wire with the heated tip mass;

said effecting step further including joining the core wire leading end and the coil tip mass into a welded assembly of respective distal ends of the coil and core wire; and removing the welded assembly from the collet to define a distal tip of the medical guidewire.

2. The process in accordance with claim 1, wherein said step of joining the core wire leading end and the heated tip mass includes passing the leading end of the core wire into the heated tip mass.

3. The process in accordance with claim 1, wherein said step of effecting relative movement includes moving the leading end of the core wire through a longitudinal passageway of the coil and generally along its axis.

4. The process in accordance with claim 1, wherein said heating step includes engaging the heated tip mass with an inside peripheral edge of the face of the collet and sealing the opening of the collet with the heated tip mass, said heating step further including precluding direct contact between the heating source and the core wire.

5. The process in accordance with claim 1, wherein said locating step is preceded by selecting an elongated core wire of an alloy composed primarily of nickel and titanium.

6. The process in accordance with claim 1, wherein said inserting step is preceded by selecting a guidewire coil made of platinum or a platinum alloy.

7. The process in accordance with claim 5, wherein said inserting step is preceded by selecting a guidewire coil made of platinum or a platinum alloy.

8. The process in accordance with claim 1, wherein said locating step is preceded by selecting an elongated core wire of stainless steel.

9. The process in accordance with claim 1, wherein said inserting step is preceded by selecting a guidewire coil made of tantalum.

10. The process in accordance with claim 1, wherein said inserting step is preceded by selecting a guidewire coil made of stainless steel.

11. The process in accordance with claim 1, further including selecting a guidewire coil having a melting point greater than the melting point of the elongated core wire.

12. The process in accordance with claim 1, further including selecting a guidewire coil having a melting point which is at least 100° C. greater than the melting point of the elongated core wire.

13. The process in accordance with claim 1, wherein said heating step includes subjecting the distal end portion of the coil to plasma arc welding.

14. A process for manufacturing, including a procedure for welding an elongated component made of an alloy of nickel and titanium as its primary components together with an assembly component having an elongated passageway, the process comprising the steps of:

inserting an assembly component having an elongated passageway into a collet to thereby support the assembly component, said inserting step including projecting a portion of the assembly component beyond a face of the collet such that said portion of the assembly is a projecting end portion which is not in engagement with the collet;

locating an elongated component made of an alloy that is primarily nickel and titanium at a staged position remote from and at a location behind the face of the collet, said elongated component having a leading end;

heating the projecting end portion of the assembly component in order to form a heated mass and continuing the heating until the heated mass engages the face of the collet;

effecting relative movement between the assembly component and the elongated component at its staged position so that the elongated component is at a location within the elongated passageway of the assembly component, said effecting step including engaging the leading end of the elongated component with the heated mass, said effecting step further including joining the elongated component leading end and the heated mass into a welded assembly; and removing the welded assembly from the collet.

15. The process in accordance with claim 14, wherein said step of joining the elongated component leading end and the heated mass includes passing the leading end of the elongated component into the heated mass.

16. The process in accordance with claim 14, wherein said heating step includes engaging the heated mass with an inside peripheral edge of the face of the collet and sealing the opening of the collet with the heated mass, said heating step further including precluding direct contact between the heating source and the elongated component.

17. The process in accordance with claim 14, wherein the elongated component is a Nitinol alloy.

18. The process in accordance with claim 14, wherein said inserting step is preceded by selecting an assembly component made of platinum or a platinum alloy.

19. The process in accordance with claim 14, further including selecting an assembly component having a melting point greater than the melting point of the elongated component.

20. The process in accordance with claim 14, further including selecting an assembly component having a melting point which is at least 100° C. greater than the melting point of the elongated component.

21. The process in accordance with claim 14, wherein said heating step includes subjecting the distal end portion of the assembly component to plasma arc welding.

* * * * *

UNITED STATES PATENT AND TRADEMARK OFFICE
CERTIFICATE OF CORRECTION

PATENT NO. : 5,488,959
DATED      : February 6, 1996
INVENTOR(S): Francisco Ales It is certified that error appears in the above-indentified patent and that said Letters Patent is hereby corrected as shown below:

Col. 3, line 65, "or-eliminate" should read --or eliminate--.
Col. 4, line 56, "Welded" should read --welded--.
Col. 6, lines 63-64, "laborintensive" should read
      --labor-intensive--.

Signed and Sealed this

Twentieth Day of August, 1996

Attest:

BRUCE LEHMAN

Attesting Officer     Commissioner of Patents and Trademarks